US008679834B2

(12) United States Patent
Lombardo et al.

(10) Patent No.: US 8,679,834 B2
(45) Date of Patent: Mar. 25, 2014

(54) METHODS AND COMPOSITIONS FOR USE IN CELLULAR THERAPIES (75) Inventors: Eleuterio Lombardo, Madrid (ES); Dirk Büscher, Madrid (ES)

(73) Assignee: TiGenix S.A.U, Tres Cantos (Madrid) (ES)

( * ) Notice: Subject to any disclaimer, the term of this patent is extended or adjusted under 35 U.S.C. 154(b) by 0 days.

(21) Appl. No.: 13/382,426

(22) PCT Filed: Jul. 9, 2010

(86) PCT No.: PCT/IB2010/001968
§ 371 (c)(1), (2), (4) Date: Apr. 18, 2012

(87) PCT Pub. No.: WO2011/004264
PCT Pub. Date: Jan. 13, 2011

(65) Prior Publication Data
US 2012/0308585 A1 Dec. 6, 2012

Related U.S. Application Data (60) Provisional application No. 61/224,275, filed on Jul. 9, 2009.

(51) Int. Cl.
*C12N 5/00* (2006.01)

(52) U.S. Cl.
USPC ........................................ 435/325

(58) Field of Classification Search
None
See application file for complete search history.

(56) References Cited

U.S. PATENT DOCUMENTS

| | | | |
|---|---|---|---|
| 2008/0159998 A1* | 7/2008 | Ichim | 424/93.21 |
| 2009/0324609 A1* | 12/2009 | Lodie et al. | 424/158.1 |
| 2011/0150845 A1* | 6/2011 | Parekkadan et al. | 424/93.7 |
| 2011/0262402 A1* | 10/2011 | Kuroda et al. | 424/93.7 |

FOREIGN PATENT DOCUMENTS

WO 2010015929 A2 2/2010

OTHER PUBLICATIONS

Marietta et al., Int. Rev. Immunol., 2011, 30: 197-206.*
Kim et al., Cell Tissue Res., 2011, 346: 53-64.*
Tay et al., Stem Cells and Development, 2012, 21: 1381-1390.*
Mackay et al., Postgraduate Medical Journal, 1988, 64: 522-530.*
Zimmerman et al., International Immunopharmacology, 2010, 10: 412-421.*
Chatenoud et al., Cold Spring Harb. Perspecs. Med., 2012, 2:a007716, 18 pages.*
Madec et al., Diabetologia, May 2009, 52: 1391-1399.*
Cao et al., Blood, 2005, 106: 3234-3241.*
Creusot et al., Blood, 2009, 113: 6638-6647.*
Hammerman, Organogenesis, 2012, 8: 41-48.*
Ben-Hur, Journal of the Neurological Sciences, 2008, 265: 102-104.*
Gonzalez, et al., "Treatment of Experimental Arthritis by Inducing Immune Tolerance With Human Adipose-Derived Mesenchymal Stem Cells," Arthritis & Rheumatism, Apr. 2009, pp. 1006-1019, vol. 60.
Zappia, et al., "Mesenchymal stem cells ameliorate experimental autoimmune encephalomyelitis inducing T-cell anergy," Blood, Sep. 2005, pp. 1755-1761, vol. 106.
Gerdoni, et al., "Mesenchymal Stem Cells Effectively Modulate Pathogenic Immune Response in Experimental Autoimmune Encephalomyelitis," Annals of Neurology, Mar. 2007, pp. 219-227, vol. 61.
Gonzalez, et al., "Adipose-Derived Mesenchymal Stem Cells Alleviate Experimental Colitis by Inhibiting Inflammatory and Autoimmune Responses," Gastroenterology, Mar. 2009, pp. 978-989, vol. 136.
Karussis, et al., "Immunomodulation and neuroprotection with mesenchymal bone marrow stem cells (MSCs): A proposed treatment for multiple sclerosis and other neuroimmunological/neurodegenerative diseases," Journal of Neurological Sciences, Jan. 2008, pp. 131-135, vol. 265.
De Vries, et al., "Magnetic resonance tracking of dendritic cells in melanoma patients for monitoring of cellular therapy," Nature Biotechnology, Nov. 2005, pp. 1407-1413, vol. 23.
Figdor, et al., "Dendritic cell immunotherapy: mapping the way," Nature Medicine, May 2004, pp. 475-480, vol. 10.
International Search Report, Written Opinion, Oct. 20, 2010.
Kuek, Annabel, et al.; Immune-mediated inflammatory diseases (IMIDs) and biologic therapy: a medical revolution, Postgrad Med J, 2007, pp. 251-260, vol. 83.
Mancheño, Pablo, et al.; "Therapeutic effect of adipose mesenchymal stem cells on experimental colitis and arthritis," TiGENIX Living Medicines, Knowledge for Growth, 2013, Research and Development Poster.
Hass, Ralf, et al.; "Different populations and sources of human mesenchymal stem cells (MSC): A comparison of adult and neonatal tissue-derived MSC," Cell Communication & Signaling, 2011, pp. 1-14, vol. 9.

* cited by examiner

*Primary Examiner* — Ilia Ouspenski
(74) *Attorney, Agent, or Firm* — Tristan A. Fuierer; Moore & Van Allen, PLLC (57) ABSTRACT

The present invention provides methods for the intralymphatic administration of cellular therapies. Further aspects of the invention provide compositions, kits and uses thereof related to such methods.

9 Claims, 1 Drawing Sheet

METHODS AND COMPOSITIONS FOR USE IN CELLULAR THERAPIES

CROSS-REFERENCE TO RELATED APPLICATIONS

This application is filed under the provisions of 35 U.S.C. §371 and claims the priority of International Patent Application No. PCT/IB2010/001968 filed on 9 Jul. 2010 entitled "Methods and Compositions for Use in Cellular Therapies" in the name of Eleuterio LOMBARDO, et al., which claims priority of U.S. Provisional Patent Application No. 61/224,275 filed on 9 Jul. 2009, both of which are hereby incorporated by reference herein in their entirety.

PURPOSE AND FIELD OF APPLICATION

The present invention relates to methods for providing cellular therapies, and therapeutic uses thereof.

BACKGROUND OF THE INVENTION

The immune system in higher vertebrates represents the first line of defence against various antigens that can enter the vertebrate body, including micro-organisms such as bacteria, fungi and viruses that are the causative agents of a variety of diseases. Moreover, the immune system is also involved in a variety of other diseases or disorders, including autoimmune or immunopathologic diseases, immunodeficiency syndromes, atherosclerosis and various neoplastic diseases. Although methods are available for treating these diseases, many current therapies provide less than adequate results. Among new emergent therapeutic strategies, those based on cell therapy appear to constitute a potentially useful tool for treating a great number of diseases. Thus, a great effort is currently being made by researchers in order to achieve said aim.

Autoimmune Diseases

Autoimmune diseases are caused when the body's immune system, which is meant to defend the body against bacteria, viruses, and any other foreign product, malfunctions and produces a pathological response against healthy tissue, cells and organs. Antibodies, T cells and macrophages provide beneficial protection, but can also produce harmful or deadly immunological responses.

Autoimmune diseases can be organ specific or systemic and are provoked by different pathogenic mechanisms. Organ specific autoimmunization is characterized by aberrant expression of major-histocompatibility complex (MHC) antigens, antigenic mimicry and allelic variations in MHC genes. Systemic autoimmune diseases involve polyclonal B cell activation and abnormalities of immunoregulatory T cells, T cell receptors and MHC genes. Examples of organ specific autoimmune diseases are diabetes, hyperthyroidism, autoimmune adrenal insufficiency, pure red cell anemia, multiple sclerosis and rheumatic carditis. Representative systemic autoimmune diseases are systemic lupus erythematosus, chronic inflammation, Sjogren's syndrome, polymyositis, dermatomyositis and scleroderma.

Current treatment of autoimmune diseases involves administering immunosuppressive agents such as cortisone, aspirin derivatives, hydroxychloroquine, methotrexate, azathioprine and cyclophosphamide or combinations thereof. The dilemma faced when administering immunosuppressive agents, however, is that the more effectively the autoimmune disease is treated, the more defenseless the patient is left to attack from infections, and also the more susceptible for developing tumours. Thus, there is a great need for new therapies for the treatment of autoimmune diseases.

Inflammatory Disorders

Inflammation is a process by which the body's white blood cells and secreted factors protect our bodies from infection by foreign substances, such as bacteria and viruses. Secreted factors known as cytokines and prostaglandins control this process, and are released in an ordered and self-limiting cascade into the blood or affected tissues.

Inflammatory Bowel Disease (IBD)

IBD is a family of chronic, idiopathic, relapsing, and tissue-destructive diseases characterized by dysfunction of mucosal T cells, altered cytokine production and cellular inflammation that ultimately leads to damage of the distal small intestine and the colonic mucosa. IBD is clinically subdivided into two phenotypes: Crohn's disease (CD) and ulcerative colitis. CD is a presently an incurable autoimmune disease with a prevalence of 0.05% that leads to chronic inflammation resulting in a range of gastrointestinal and extraintestinal symptoms, including abdominal pain, rectal bleeding, diarrhea, weight loss, skin and eye disorders, and delayed growth and sexual maturation in children. These symptoms can greatly impact the patients' well being, quality of life, and capacity of function. Because CD is chronic and typically has an onset before 30 years of age, patients generally require lifelong treatment. Although its etiology remains unknown, there is circumstantial evidence to link CD to a failure of the mucosal immune system to attenuate the immune response to endogenous antigens.

Therapeutic agents currently used for CD, including aminosalicylates, corticosteroids, azathioprine, 6-mercaptopurine, antibiotics, and methotrexate, are not entirely effective, are nonspecific, and have multiple adverse side effects. In most cases, surgical resection is the ultimate alternative. Therefore, the present therapeutic strategy is to find drugs or agents that specifically modulate both components of the disease, i.e., the inflammatory and T-cell driven responses.

Recently, the drug infliximab has been approved for the treatment of moderate to severe Crohn's disease that does not respond to standard therapies and for the treatment of open, draining fistulas. Infliximab, the first treatment approved specifically for Crohn's disease, is an anti-tumour necrosis factor (TNF) antibody. TNF is a protein produced by the immune system that may cause the inflammation associated with Crohn's disease. Anti-TNF removes TNF from the bloodstream before it reaches the intestines, thereby preventing inflammation. However, since it has a systemic effect, and TNF is a very pleiotropic factor, severe side effects are relatively common, and its long-term safety is still to be determined. Also, the efficacy is also limited because many of the inflammatory processes that occur in the patients are not dependant on TNF signalling.

Rheumatoid Arthritis (RA)

Rheumatoid arthritis and juvenile rheumatoid arthritis are types of inflammatory arthritis. Arthritis is a general term that describes inflammation in joints. Some, but not all, types of arthritis are the result of misdirected inflammation. Rheumatoid arthritis affects about 1% of the world's population and is essentially disabling. Rheumatoid arthritis is an autoimmune disorder whereby the body's immune system improperly identifies the synovial membranes that secrete the lubricating fluid in the joints as foreign. Inflammation results, and the cartilage and tissues in and around the joints are damaged or destroyed. The body replaces damaged tissue with scar tissue, causing the normal spaces within the joints to become narrow and the bones to fuse together.

In rheumatoid arthritis, there is an autoimmune cycle of persistent antigen presentation, T-cell stimulation, cytokine secretion, synovial cell activation, and joint destruction.

Current therapies for arthritis focus on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. Anti-TNF humanized monoclonal antibodies, such as Infliximab are also used, however, it has many secondary effects or side effects and its efficacy is quite low. "Second line drugs" include gold, methotrexate and steroids. Although these are well-established treatments for arthritis, very few patients remit on these lines of treatment alone, and difficult treatment issues still remain for patients with rheumatoid arthritis.

In general, the current treatments for chronic inflammatory disorders have a very limited efficiency, and many of them have a high incidence of side effects or cannot completely prevent disease progression. So far, no treatment is ideal, and there is no cure for these type of pathologies. Thus, there is a great need for new therapies for the treatment of inflammatory disorders.

SUMMARY OF THE INVENTION

The present invention provides improved methods for the cellular therapy of patients in need thereof. Further aspects of the invention provide kits and compositions for use in an intralymphatically delivered cellular therapy.

In one aspect, a method for treating or repairing damaged tissue, and/or for the treatment, modulation, prophylaxis, and/or amelioration of one or more symptoms associated with inflammatory and/or immune disorders, having damaged tissue and/or one or more symptoms associated with inflammatory and/or immune disorders is described, which comprises administering to the lymphatic system of said subject a prophylactically or therapeutically effective amount of a composition comprising stem cells, regulatory T-cells and/or fibroblast cells. In one embodiment the present invention provides a method of preventing, treating, or ameliorating immune and/or inflammatory disease in an individual comprising direct delivery of a cellular therapy to a lymphatic organ. In one embodiment of the invention the cellular therapy is delivered in combination with an antigen.

In another aspect, a stem cell, regulatory T-cell and/or fibroblast cell is described, for use in a method of:
 i. treating or repairing damaged tissue; and/or
 ii. treating, modulating, ameliorating and/or prophylaxis of one or more symptoms associated with inflammatory and/or immune disorders;
wherein the cell is administered to the lymphatic system.

In yet another aspect, a kit is described, said kit comprising i) a medicament comprising of a stem cell, regulatory T-cell and/or fibroblast population and ii) instructions for a method for treating or repairing damaged tissue, and/or for the treatment, modulation, prophylaxis, and/or amelioration of one or more symptoms associated with inflammatory and/or immune disorders, in a subject in need of such treatment is described, which comprises administering to the lymphatic system of said subject a prophylactically or therapeutically effective amount of a composition comprising stem cells, regulatory T-cells and/or fibroblast cells.

In still another aspect, the use of a stem cell, regulatory T-cell and/or a fibroblast cell in the manufacture of a medicament for treating or repairing damaged tissue, and/or for the treatment, modulation, prophylaxis, and/or amelioration of one or more symptoms associated with inflammatory and/or immune disorders is described, said use comprising the administration of the stem cell, regulatory T-cell and/or fibroblast cell into the lymphatic system.

Another aspect relates to a stem cell, regulatory T-cell or fibroblast for administration to the lymphatic system. Yet another aspect relates to that cell for use in therapy.

Still another aspect relates to a pharmaceutical composition for administration to the lymphatic system comprising a stem cell, regulatory T-cell and/or a fibroblast, and an antigen.

Other aspects, features and advantages will be more fully apparent from the ensuing disclosure and appended claims.

DEFINITIONS

In order to facilitate the understanding of the present description, the meaning of some terms and expressions in the context of the invention will be explained below. Further definitions will be included throughout the description as necessary.

The terms "adapted for intralymphatic injection" or "adapted for intranodal injection" or "adapted for direct injection into the axillary and/or inguinal lymph node" according to the invention means that the cellular therapy, preferably comprising immunomodulatory cells, most preferably comprising stem cells, regulatory T-cells and/or fibroblast cells, as well as medicaments and pharmaceutical compositions comprising same, adapted for intralymphatic or intranodal injection has physical, chemical, biological and other characteristics necessary or beneficial for injecting same as a medical treatment into lymphatic tissue of an individual, especially a human, even more preferably a human patient for the treatment or repair of damaged tissue (preferably mesenchymal tissue), and/or for the treatment, modulation, prophylaxis, and/or amelioration of one or more symptoms associated with inflammatory and/or immune disorders in a subject in need of such treatment. Furthermore immunomodulatory cells, as well as medicaments and pharmaceutical compositions comprising same "adapted for intralymphatic injection" or "adapted for intranodal injection" according to the invention contain concentrations of all constituents of the composition allowing the application of appropriate amounts of all constituents in an appropriate volume into lymphatic tissue, preferably a volume of up to 0.01, preferably up to 0.05, preferably up to 0.1, preferably up to 0.2, preferably up to 0.3, preferably up to 0.4, preferably up to 0.6, preferably up to 0.8, preferably up to 1.0, preferably up to 2 mL. Furthermore compositions "adapted for intralymphatic or intranodal injection" should contain no or only limited amounts of potential harmful substances such as solvents and adjuvants, which might damage lymphatic tissue, if applied in too large quantities. With damage of lymphatic tissue is meant direct damage due to toxic effects to cells, due to chemical destruction of cells, due to indirect damage to cells for example by inducing inflammatory reactions, necrosis, etc.

Furthermore a composition "adapted for intralymphatic or intranodal injection" according to the invention ideally has some kind of safety-mechanism, which prevents accidental, systemic application of the immunomodulatory cells, as well as medicaments and pharmaceutical compositions comprising same, in case the injection misses the lymphatic tissue and in the worst case results in direct injection of the immunomodulatory cells, as well as medicaments and pharmaceutical compositions comprising same into the blood circulation. Such a safety-mechanism includes a short extracellular half-life of the biological active substances.

The term "injection" as used herein is to be given its usual meaning in the art, referring to the delivery of an agent to the body by piercing part of the body, usually the skin. The term includes the use of hollow syringes and high-pressure jet injection devices.

The term "allogeneic" as used herein shall be taken to mean from different individuals of the same species. Two or more individuals are said to be allogeneic to one another when the genes at one or more loci are not identical.

The term "autologous" as used herein shall be taken to mean from the same individual.

The term "immune disease" refers to a condition in a subject characterized by cellular, tissue and/or organ injury caused by an immunological reaction of the subject. The term "autoimmune disease" refers to a condition in a subject characterized by cellular, tissue and/or organ injury caused by an immunological reaction of the subject to its own cells, tissues and/or organs. Illustrative, non-limiting examples of autoimmune diseases which can be treated with the immunomodulatory cells of the invention include alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiffman syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, Anti-Glomerular Basement Membrane Disease, Antiphospholipid Syndrome, Autoimmune Diseases of the Nervous System, Familial Mediterranean Fever, Lambert-Eaton Myasthenic Syndrome, Sympathetic Ophthalmia, Polyendocrinopathies, Psoriasis, etc.

The term "Immune Mediated inflammatory Disease" shall be taken to mean any disease characterized by chronic or acute inflammation, resulting from, associated with or triggered by, a dysregulation of the normal immune response e.g. Crohn's disease, type 1 diabetes mellitus, rheumatoid arthritis, inflammatory bowel disease, psoriasis, psoriatic arthritis, ankylosing spondylitis, systemic lupus erythematosus, Hashimoto's disease, graft-versus-host disease, Sjogren's syndrome, pernicious anemia, Addison disease, scleroderma, Goodpasture's syndrome, ulcerative colitis, autoimmune hemolytic anemia, sterility, myasthenia gravis, multiple sclerosis, Basedow's disease, thrombopenia purpura, Guillain-Barré syndrome, allergy, asthma, atopic disease, arteriosclerosis, myocarditis, cardiomyopathy, glomerular nephritis, hypoplastic anemia, and rejection after organ transplantation.

"Celiac disease" is alternatively referred to as coeliac disease, c(o)eliac sprue, non-tropical sprue, endemic sprue, gluten enteropathy or gluten-sensitive enteropathy, and gluten intolerance.

For the purposes of the invention described herein, "immune disorders" include autoimmune diseases and immunologically mediated diseases.

The term "inflammatory disease" refers to a condition in a subject characterized by inflammation, e.g., chronic inflammation. Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The term "isolated" applied to a cell population refers to a cell population, isolated from the human or animal body, which is substantially free of one or more cell populations that are associated with said cell population in vivo or in vitro. The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably. The term "subject" refers to an animal, preferably a mammal including a non-primate (e.g., a cow, pig, horse, cat, dog, rat, or mouse) and a primate (e.g., a monkey, or a human). In a preferred embodiment, the subject is a human.

The term "immunomodulatory" refers to the inhibition or reduction of one or more biological activities of the immune system which includes, but is not limited to, downregulation of immune response and inflammatory states as well as changes in cytokine profile, cytotoxic activity and antibody production. The term "antigen specific immunomodulatory" refers to the inhibition or reduction of one or more biological activities of the immune system associated with a specific antigen or antigens, including both alloantigens and autoantigens. The term "immunomodulatory" shall be taken to comprise "antigen specific immunomodulatory".

As used herein, "negative" or "−" as used with respect to cell surface markers shall be taken to mean that mean that, in a cell population, less than 20%, 10%, preferably less than 9%, 8%, 7%, 6%, 5%, 4%, 3%, 2%, 1% or none of the cells express said marker. Expression of cell surface markers may be determined for example by means of flow cytometry for a specific cell surface marker using conventional methods and apparatus (for example a Beckman Coulter Epics XL FACS system used with commercially available antibodies and standard protocols known in the art).

As used herein, the term "lymphatic system" is to be given its usual meaning in the art and refers to lymphoid tissue connected by a conducting system of lymph vessels and lymph capillaries. The term "lymphatic organ" refers to lymph nodes, most preferably an axillary or inguinal lymph node, or for those individuals lacking lymph nodes or having defects thereof, lymphatic tissue or an immune cell.

As used herein the term "mesenchymal stem cell" (also referred to herein as "MSC") shall be taken to mean a cell which is capable of giving rise to multiple different types of cell, originally derived from the mesenchyme. The term refers to a cell which is capable of differentiating into at least one of an osteoblast, a chondrocyte, an adipocyte, or a myocyte. MSCs may be isolated from any type of tissue. Generally MSCs will be isolated from bone marrow, adipose tissue, umbilical cord, or peripheral blood. The MSCs used in the invention may in some embodiments be isolated from bone marrow (BM-MSCs) or adipose tissue (ASCs). In a preferred aspect of the invention, MSCs are obtained from lipoaspirates, themselves obtained from adipose tissue.

As used herein, the expression "significant expression" or its equivalent terms "positive" and "+" when used in regard to a cell surface marker shall be taken to mean that, in a cell population, more than 20%, preferably more than, 30%, 40%, 50%, 60%, 70%, 80%, 90% 95%, 98%, 99% or even all of the cells of the cells express said marker.

Expression of cell surface markers may be determined for example by means of flow cytometry for a specific cell surface marker using conventional methods and apparatus (for example a Beckman Coulter Epics XL FACS system used with commercially available antibodies and standard protocols known in the art) that show a signal for a specific cell surface marker in flow cytometry above the background signal using conventional methods and apparatus (for example, a Beckman Coulter Epics XL FACS system used with commercially available antibodies and standard protocols known in the art). The background signal is defined as the signal intensity given by a non-specific antibody of the same isotype as the specific antibody used to detect each surface marker in conventional FACS analysis. For a marker to be considered positive the specific signal observed is stronger than 20%, preferably stronger than, 30%, 40%, 50%, 60%, 70%, 80%, 90%, 500%, 1000%, 5000%, 10000% or above, than the background signal intensity using conventional methods and apparatus (for example a Beckman Coulter Epics XL FACS system used with commercially available antibodies and standard protocols known in the art).

Furthermore, commercially available and known monoclonal antibodies against said cell-surface markers (e.g., cellular receptors and transmembrane proteins) can be used to identify relevant cells.

The term "connective tissue" refers to tissue derived from mesenchyme and includes several tissues which are characterized in that their cells are included within the extracellular matrix. Examples of connective tissues include but are not limited to, adipose and cartilaginous tissues.

The term "fibroblast" as used herein shall be taken to include fibroblast like synovial cells.

The term "T-cell" refers to cells of the immune system which are a subset of lymphocytes that express the T cell receptor (TCR). The term "regulatory T-cells" (also referred to herein as T-reg cells) refers to T cell subsets that actively suppress activation of the immune system and prevent pathological self-reactivity, i.e. an autoimmune disease. The term "regulatory T-cells" or "T-reg cells" shall be taken to include both naturally occurring t-cells (FoxP3+T-reg cells) and adaptive T-cells (also known as Tr1 cells or Th3 cells) which do not express the FoxP3 molecule.

The term "gluten" shall be taken to mean a protein comprising gliadin and glutenin components.

As used herein, the terms "treat", "treatment" and "treating" when used directly in reference to a patient or subject shall be taken to mean the amelioration of one or more symptoms associated with a disorder including, but not limited to, an inflammatory disorder, an autoimmune disease or an immunologically mediated disease including rejection of transplanted organs and tissues, wherein said amelioration results from the administration of the immunomodulatory cells of the invention, or a pharmaceutical composition comprising same, to a subject in need of said treatment.

As used herein the terms "repair" and "repairing" when used directly in reference to damaged tissues shall be taken to mean the amelioration of such damage by both direct mechanisms such as the regeneration of damaged tissues, as well as through indirect mechanisms e.g., reducing inflammation thereby enabling tissue formation.

The term "combination therapy" refers to the use of the immunomodulatory cells of the present invention or pharmaceutical compositions comprising same together with other active agents or treatment modalities, in the manner of the present invention for the amelioration of one or more symptoms associated with a disorder including, but not limited to, an inflammatory disorder, an autoimmune disease or an immunologically mediated disease including rejection of transplanted organs and tissues. These other agents or treatments may include known drugs and therapies for the treatment of such disorders such as but not limited to corticosteroids and non-steroidal anti-inflammatory compounds.

The immunomodulatory cells of the invention, or pharmaceutical compositions comprising same may also be combined with other treatment modalities, e.g., corticosteroids, non-steroidal anti-inflammatory compounds, or other agents useful in treating inflammation. The combined use of the agents of the present invention with these other therapies or treatment modalities may be concurrent, or given sequentially, that is, the two treatments may be divided up such that said immunomodulatory cells or a pharmaceutical composition comprising same may be given prior to or after the other therapy or treatment modality. The attending physician may decide on the appropriate sequence of administering the immunomodulatory cells, or a pharmaceutical composition comprising same, in combination with other agents, therapies or treatment modalities.

DESCRIPTION OF THE INVENTION

In one aspect the present invention provides a method for treating or repairing damaged tissue (preferably mesenchymal tissue), and/or for the treatment, modulation, prophylaxis, and/or amelioration of one or more symptoms associated with inflammatory and/or immune disorders in a subject in need of such treatment, which comprises administering to the lymphatic system of said subject a prophylactically or therapeutically effective amount of a composition comprising a cellular therapy. Accordingly, in a further aspect, the present invention provides a cellular therapy, preferably comprising immunomodulatory cells, most preferably comprising stem cells, regulatory T-cells and/or fibroblast cells for use in treating or repairing damaged tissue (preferably mesenchymal tissue), and/or for the treatment, modulation, prophylaxis, and/or amelioration of one or more symptoms associated with inflammatory and/or immune disorders, wherein the cellular therapy is administered to the lymphatic system. The intralymphatic administration is preferably carried out by intralymphatic injection. The cellular therapy is adapted for intralymphatic administration, preferably intralymphatic injection.

The administration of stem cells, regulatory T-cells and/or fibroblast cells directly into the lymphatic system has several advantages over the prior art, namely over conventional subcutaneous injection of said stem cells, regulatory T-cells and/or fibroblast cells, for example, a lower amount of immunomodulatory cells is sufficient; the therapy is no more painful to the patient than regular subcutaneous injections; and there are less adverse side effects. Moreover, by direct application to the lymphatic tissue, for example by intranodal injection, the immunomodulatory cells are delivered closer to the site of treatment or repair of the damaged tissue.

Immunomodulatory cells, as well as medicaments and pharmaceutical compositions comprising same, according to the present invention may, simultaneously with the intralymphatic administration, be administered by conventional routes, like subcutaneous administration or sublingual administration, orally, transcutaneously (topical vaccination), intradermally, intramedullary, intrathecal, intraventricular, intranasally, conjunctival, intrabronchial, transdermally, intrarectally, intraperitoneally, intramuscularly, intrapulmonary, vaginally, rectally, or intraocularly.

It is preferred that the cellular therapy according to the present invention comprises stem cells, regulatory T-cells and/or fibroblast cells. It is particularly preferred that said stem cells are mesenchymal stem cells (hereinafter also referred to as MSC), most preferably adipose derived mesenchymal stem cells (hereinafter also referred to as ASC), which are MSCs that originate from adipose tissue, generally from human adipose tissue (hASCs).

The fibroblasts used in the present invention are mesenchyme derived connective tissue that are associated with the synthesis and maintenance of extra cellular matrix and shall be taken to include fibroblast like synovial cells. The fibroblasts can be obtained from any suitable animal, most preferably human.

The regulatory T-cells (sometimes known as suppressor T-cells) as used in the present invention may be derived from any suitable source, such as blood or spleen. The regulatory T-cells may be naturally occurring CD4$^+$Foxp3$^+$ cells, or they may be ex-vivo isolated and/or expanded regulatory T-cells. Methods for the ex-vivo expansion of regulatory T-cells are known in the art and include the isolation from whole blood (e.g., as part of the PBMC fraction) followed by expansion using e.g., mesenchymal stem cells or Rapamycin.

The MSC used in the method of the present invention are preferably derived from connective tissue. In a preferred embodiment said MSC are derived from adipose tissue and in a further preferred embodiment from the stromal fraction of the adipose tissue. In an alternative embodiment, said MSC are obtained from chondrocytes of the hyaline cartilage. In a further embodiment, said MSC are obtained from skin. In another embodiment, said MSC are obtained from bone marrow.

The MSC can be obtained from any suitable source of connective tissue from any suitable animal, most preferably humans. It is preferred that said cells are obtained from non-pathological mammalian sources, preferably post-natal (e.g., rodent or primate) sources. In a preferred embodiment, the MSC are obtained from a source of connective tissue, such as, but not limited to, the stromal fraction of adipose tissue, hyaline cartilage, bone marrow or skin. Most preferably the MSC of the methods of the present invention are obtained from non-pathological, post-natal, human stromal adipose tissue.

With respect to the intended recipient of the immunomodulatory cells as administered according to the method of the present invention, the MSC, regulatory T-cells and/or fibroblast cells used in said above described method may be of either allogeneic (donor) or autologous (subject) origin. In one embodiment of the method said MSC, regulatory T-cells and/or fibroblast cells are of allogeneic origin. In one embodiment of the method said MSC, regulatory T-cells and/or fibroblast cells are of autologous origin.

The MSC, regulatory T-cells and/or fibroblast cells used in the method of the present invention are preferably characterized in that (i) they do not express markers specific for antigen presenting cells, (ii) they do not express IDO (Indoleamine 2,3-Dioxygenase) constitutively, (iii) they express IDO upon stimulation with IFN-gamma, and in the case of MSC (iv) they present the capacity to be differentiated into at least two cell lineages.

The stem cells, regulatory T-cells and/or fibroblast cells according to the present invention are preferably delivered in a physiologically acceptable carrier suitable for injection. In general, any physiologically acceptable carrier known for use can be used in the practice of this invention. The choice of such carriers includes, without limitation, Ringer's solution, water, standard saline solutions, dextrose solutions and albumin water, and is easily within the skill of the art.

Optionally, the lymphatic system or a part thereof, for example a localized area of a lymph vessel or a lymph organ, preferably a lymph node, may be visualized during the injection procedure. Ultrasound, radiological, or other visualization means such as computerized axial tomography (CAT scan), can be used to visualize the lymph node and monitor location of the needle and changes in the lymph node, such as swelling. Injection into the axillary and inguinal lymph nodes is preferred due to ease of ultrasound guided location and injection.

The technique used for injection is within the skill of the art. One method is to use a single chamber syringe containing the cells in liquid formulation.

In another aspect, the present invention provides a method for treating or repairing damaged tissue (preferably mesenchymal tissue), and/or for the treatment, modulation, prophylaxis, and/or amelioration of one or more symptoms associated with inflammatory and/or immune disorders, in a subject in need of such treatment, comprising administering to the lymphatic system of said subject a prophylactically or therapeutically effective amount of a composition comprising a cellular therapy (most preferably comprising of MSC, regulatory T-cells and/or fibroblasts) and further comprising the administration of an antigen directly to the lymphatic system of said subject. Said antigen may be administered prior to, concurrently with or subsequent to the administration of the cellular therapy. The antigen may be administered at least 1, 2, 3, 5 or 10 hours prior or subsequent to the administration of the cellular therapy.

The antigen used in said methods may be a chosen antigen, group of antigens or cell types expressing and/or presenting said antigen or antigens. In one embodiment the antigen is selected from a group comprising: a mixture of autoantigens derived from a patient suffering with autoimmunity, a peptide antigen, a nucleic acid, an altered peptide ligand, a recombinant protein or fragments thereof. In one embodiment said antigens are associated with arthritis (such as but not limited to collagen antigens). In an alternative embodiment said antigens are associated with celiac disease. Antigens associated with celiac disease are members of the gluten family including some forms of prolamins (such as but not limited to antigens of gliadins, hordeins, and/or secalins). In a further embodiment said antigens are associated with multiple sclerosis (such as but not limited to myelin antigens). Methods for the isolation, purification and preparation of such antigens are known to the person skilled in the art.

It is particularly preferred that the cellular therapy of all aspects of the present invention is administered directly to a lymphatic organ, most preferably a peripheral lymphatic organ, including but not limited to the lymph nodes, most preferably an axillary or inguinal lymph node. In individuals lacking lymph nodes or having defects thereof, the cellular therapy may be delivered to the lymphatic tissue or to an immune cell.

Methods for intralymphatic administration are known in the art and are commonly carried out by means of an injection device (e.g., syringe). The administration may be aided and observed by means of an imaging device such as but not limited to a radiological, ultrasound and computerized axial tomography (CAT scan). This allows the precise administration of the cellular therapy and also the monitoring of the lymphatic organs for adverse events. In one aspect of the method the subject is treated with a plurality of doses of the intralymphatically administered cellular therapy. Preferably at least 2, 3, 4, 5, 10 or 15 doses are administered at intervals. In a further aspect of the method each of said doses comprises between 10,000 and 5,000,000 cells. In a further embodiment each of said doses comprises of between 10,000 and 100,000 cells; 100,000 and 500,000 cells; 500,000 and 1,000,000 cells or between 1,000,000 and 5,000,000 cells.

In still another aspect, the present invention provides a stem cell, regulatory T-cells and/or fibroblast cell for administration to the lymphatic system.

In another aspect the present invention provides the use of a stem cell, regulatory T-cell and/or a fibroblast cell as a medicament for treating or repairing damaged tissue (preferably mesenchymal tissue), and/or for the treatment, modulation, prophylaxis, and/or amelioration of one or more symptoms associated with inflammatory and/or immune disorders, by administration of the stem cell, regulatory T-cell and/or fibroblast cell into the lymphatic system.

An alternative aspect of the present invention provides the use of a stem cell, regulatory T-cells and/or a fibroblast cell in the manufacture of a medicament for treating or repairing damaged tissue (preferably mesenchymal tissue), and/or for the treatment, modulation, prophylaxis, and/or amelioration of one or more symptoms associated with inflammatory and/or immune disorders, by administration of the stem cell, regulatory T-cell and/or fibroblast cell into the lymphatic system.

In a further aspect the present invention provides a pharmaceutical composition for administration to the lymphatic system comprising stem cells, regulatory T-cells and/or fibroblasts. Said pharmaceutical compositions are of use in the treatment, repair, prophylaxis, and/or amelioration of damaged tissues, or one or more symptoms associated with inflammatory and/or immune disorders such as but not limited to autoimmune diseases, inflammatory disorders, and immunologically mediated diseases including rejection of transplanted organs and tissues. In one embodiment of the invention the pharmaceutical composition may further comprise an antigen, group of antigens or cell types expressing and/or presenting said antigen or antigens. In one embodiment the antigen is selected from a group comprising of: a mixture of autoantigens derived from a patient suffering with autoimmunity, a peptide antigen, a nucleic acid, an altered peptide ligand, a recombinant protein or fragments thereof. In one embodiment said antigens are associated with arthritis, such as but not limited to collagen antigens. In an alternative embodiment said antigens are associated with Celiac Disease. Antigens associated with celiac disease are members of the gluten family including some forms of prolamins (such as but not limited to antigens of gliadins, hordeins, and/or secalins). Gluten and its components, glutanin and gliadin, are preferred antigens associated with Celiac disease. In a further embodiment said antigens are associated with multiple sclerosis, such as but not limited to myelin antigens and myelin component antigens such as myelin basic protein (MBP), myelin oligodendrocyte glycoprotein (MOG), proteolipid protein (PLP) and myelin glycolipids e.g. galactocerebroside. Methods for the isolation, purification and preparation of such antigens are known to the person skilled in the art.

The pharmaceutical composition of the invention comprises a prophylactically or therapeutically effective amount of stem cells, regulatory T-cells and/or fibroblasts, optionally antigen, and a pharmaceutical carrier. Examples of dosages and dosage regimes for each of these cell types are given above. Suitable pharmaceutical carriers are known in the art and are preferably those approved by a regulatory agency of the US Federal or a state government or listed in the US Pharmacopeia, or European Pharmacopeia, or other generally recognized pharmacopeia for use in animals, and more particularly in humans. The term "carrier" refers to a diluent, adjuvant, excipient, or vehicle with which the therapeutic agent is administered. The composition, if desired, can also contain minor amounts of pH buffering agents. Examples of suitable pharmaceutical carriers are described in "Remington's Pharmaceutical Sciences" by E W Martin. Such compositions will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, semi-solid, and liquid dosage forms, such as lyophilized preparations, liquid solutions or suspensions, injectable and infusible solutions, etc. As noted above, the pharmaceutical composition is preferably injectable.

It is preferred that the methods, medicaments, compositions and cells of the invention are used for treating or repairing damaged tissue (preferably mesenchymal tissue), and/or for the treatment, modulation, prophylaxis, and/or amelioration of one or more symptoms associated with inflammatory and/or immune disorders. Accordingly the methods and cells of the invention are of use in the treatment of any disorder characterized by either or all of said symptoms. A representative non-exhaustive list of such disorders is provided in the definitions section. Particularly preferred is the use of the methods, medicaments, compositions and cells of the invention in the treatment of immune-mediated inflammatory diseases. Further preferred is the use of the methods, medicaments, compositions and cells of the invention in the treatment of diabetes mellitus, rheumatoid arthritis (RA), inflammatory bowel disease (IBD, including Crohn's disease and/or Ulcerative Colitis) and multiple sclerosis (MS). Even more particularly preferred is the use of the methods, medicaments, compositions and cells of the invention in the treatment of rheumatoid arthritis.

Wherein the method or composition of the invention comprises one or more antigens it is preferred that the method or composition is used in the treatment of the disorder associated with or induced by said antigen, for example wherein the antigen is collagen the method or composition may be used in the treatment of arthritis, wherein the antigen is a gluten component the methods or compositions may be used in the treatment of celiac disease, wherein the antigen is a myelin component the methods or compositions may be used to treat multiple sclerosis. Preferred compositions therefore comprise: MSC, preferably ASC, and collagen, for the treatment of arthritis; MSC, preferably ASC, and gluten and/or a gluten component, for the treatment of celiac disease; MSC, preferably ASC, and myelin and/or a myelin component, for the treatment of multiple sclerosis.

In a further aspect the present invention provides a kit comprising i) a medicament comprising of a stem cell, regulatory T-cell and/or fibroblast population and ii) instructions for the use thereof according to the methods of the present invention.

In a further embodiment said kit may further comprise of iii) one or more antigens.

MSC Phenotype Markers.

The MSC used in a preferred method of the present invention are preferably negative for markers associated with APC (Antigen Presenting Cell) phenotypes. Accordingly it is preferred that said MSC are negative for at least one, two, three, four or preferably all of the following markers: CD 11b; CD 11c; CD14; CD45; HLAII. Furthermore, the MSC are preferably negative for at least one, two, or preferably all of the following cell surface markers: CD31; CD34; CD 133.

In a particular embodiment, the MSC as used in the present method are preferably characterised in that they express (i.e., are positive for) at least one, two, three, four, of or preferably all of the following cell surface markers CD9, CD44, CD54, CD90 and CD 105. Preferably, the MSC are characterised in that they have significant expression levels of at least one, two, three, four, of and preferably all of said cell surface markers CD9, CD44, CD54, CD90 and CD 105.

Optionally, the MSC may also be negative for the cell surface marker CD 106 (VCAM-1). Examples of MSC suitable for use in the method of the present invention are described in the art, for example in WO2007039150, which is hereby incorporated by reference in its entirety.

Differentiation.

The MSC suitable for use in the method of the present invention are preferably multipotent or pluripotent stem cells and may present the capacity to proliferate and be differentiated into at least two, more preferably three, four, five, six, seven or more cell lineages. Illustrative, non-limiting examples of cell lineages into which said MSC can be differentiated include osteocytes, adipocytes, chondrocytes, tenocytes, myocytes, cardiomyocytes, hematopoietic-supporting stromal cells, endothelial cells, neurons, astrocytes, and hepatocytes. MSC can proliferate and differentiate into cells of other lineages by conventional methods. Methods of identifying and subsequently isolating differentiated cells from their undifferentiated counterparts can be also carried out by methods well known in the art.

MSC Isolation

Methods for the isolation of MSC are known in the art, and any suitable method may be used. In one embodiment isolation of ASC this may comprise the steps of:

(i) preparing a cell suspension from a sample of adipose;
(ii) recovering the cells from said cell suspension;
(iii) incubating said cells in a suitable cell culture medium on a solid surface under conditions which allow cells to adhere to the solid surface and proliferate;
(iv) washing said solid surface after incubation to remove non-adhered cells;
(v) selecting the cells which after being passaged at least twice in such medium remain adhered to said solid surface; and
(vi) confirming that the selected cell population presents the phenotype of interest.

As used herein, the term "solid surface" refers to any material upon which the ASC can adhere. In a particular embodiment said material is a plastic material treated to promote the adhesion of mammalian cells to its surface, for example commercially available polystyrene plates optionally coated with poly-D-Lysine or other reagents.

Steps (i)-(vi) can be carried out by conventional techniques known by those skilled in the art. Briefly, the ASC can be obtained by conventional means from any suitable source of connective tissue from any suitable animal as discussed above. Typically, human adipose cells are obtained from living donors, using well-recognized protocols such as surgical or suction lipectomy. Indeed, as liposuction procedures are so common, liposuction effluent is a particularly preferred source from which the ASC can be derived. Thus, in a particular embodiment, the ASC are from the stromal fraction of human adipose tissue obtained by liposuction.

The tissue is, preferably, washed before being processed to separate the ASC from the remainder of the material. In one commonly used protocol, the sample of tissue is washed with physiologically-compatible saline solution (e.g., phosphate buffered saline (PBS)) and then vigorously agitated and left to settle, a step that removes loose matter (e.g., damaged tissue, blood, erythrocytes, etc) from the tissue. Thus, the washing and settling steps are generally repeated until the supernatant is relatively clear of debris. The remaining cells generally will be present in clumps of various sizes, and the protocol proceeds using steps gauged to degrade the gross structure while minimizing damage to the cells themselves. One method of achieving this end is to treat the washed lumps of cells with an enzyme that weakens or destroys bonds between cells (e.g., collagenase, dispase, trypsin, etc.). The amount and duration of such enzymatic treatment will vary, depending on the conditions employed, but the use of such enzymes is generally known in the art. Alternatively, or in conjunction with such enzymatic treatment, the lumps of cells can be degraded using other treatments, such as mechanical agitation, sonic energy, thermal energy, etc. If degradation is accomplished by enzymatic methods, it is desirable to neutralize the enzyme following a suitable period, to minimize deleterious effects on the cells.

The degradation step typically produces a slurry or suspension of aggregated cells and a fluid fraction containing generally free stromal cells (e.g., red blood cells, smooth muscle cells, endothelial cells, fibroblast cells, and stem cells). The next stage in the separation process is to separate the aggregated cells from the ASC. This can be accomplished by centrifugation, which forces the cells into a pellet covered by a supernatant. The supernatant then can be discarded and the pellet suspended in a physiologically-compatible fluid. Moreover, the suspended cells typically include erythrocytes, and in most protocols it is desirable to lyse them. Methods for selectively lysing erythrocytes are known in the art, and any suitable protocol can be employed (e.g., incubation in a hyper- or hypotonic medium, by lysis using ammonium chloride, etc.). Of course, if the erythrocytes are lysed, the remaining cells should then be separated from the lysate, for example by filtration, sedimentation, or density fractionation.

Regardless of whether the erythrocytes are lysed, the suspended cells can be washed, re-centrifuged, and resuspended one or more successive times to achieve greater purity. Alternatively, the cells can be separated on the basis of cell surface marker profile or on the basis of cell size and granularity.

Following the final isolation and re-suspension, the cells can be cultured and, if desired, assayed for number and viability to assess the yield. Preferably, the cells will be cultured without differentiation, on a solid surface, using a suitable cell culture media, at the appropriate cell densities and culture conditions. Thus, in a particular embodiment, cells are cultured without differentiation on a solid surface, usually made of a plastic material, such as Petri dishes or cell culture flasks, in the presence of a suitable cell culture medium [e.g., DMEM, typically supplemented with 5-15% (e.g., 10%) of a suitable serum, such as fetal bovine serum or human serum], and incubated under conditions which allow cells to adhere to the solid surface and proliferate. After incubation, cells are washed in order to remove non-adhered cells and cell fragments. The cells are maintained in culture in the same medium and under the same conditions until they reach the adequate confluence, typically, about 70%, about 80% or about 90% cell confluence, with replacement of the cell culture medium when necessary. After reaching the desired cell confluence, the cells can be expanded by means of consecutive passages using a detachment agent such as trypsin and seeding onto a new cell culture surface at an appropriate cell density (usually 2,000-10,000 cells/cm$^2$). Thus, cells are then passaged at least two times in such medium without differentiating, while still retaining their developmental phenotype, and more preferably, the cells can be passaged at least 10 times (e.g., at least 15 times or even at least 20 times) without losing developmental phenotype. Typically, the cells are plated at a desired density such as between about 100 cells/cm$^2$ to about 100,000 cells/cm$^2$ (such as about 500 cells/cm$^2$ to about 50,000 cells/cm$^2$, or, more particularly, between about 1,000 cells/cm$^2$ to about 20,000 cells/cm$^2$). If plated at lower densities (e.g., about 300 cells/cm$^2$), the cells can be more easily clonally isolated. For example, after a few days, cells plated at such densities will proliferate into a homogeneous population. In a particular embodiment, the cell density is between 2,000-10,000 cells/cm$^2$.

Cells which remain adhered to the solid surface after such treatment comprising at least two passages are selected and the phenotype of interest is analyzed by conventional methods in order to confirm the identity of the ASC as will be mentioned below. Cells which remain adhered to the solid surface after the first passage are from heterogeneous origin; therefore, said cells must be subjected to at least another passage. As a result of the above method, a homogeneous cell population having the phenotype of interest is obtained. The adhesion of cells to the solid surface after at least two passages constitutes a preferred embodiment of the invention for selecting the ASC. Confirmation of the phenotype of interest can be carried out by using conventional means.

Preferably said expansion is carried out by duplication or triplication of said population at least 1, at least 2, at least 3, at least 4, at least 5, at least 10, at least 15 or at least 20 times. In a further embodiment said expansion is carried over at least 1, at least 2, at least 3, at least 4, at least 5, at least 10, at least 15 or at least 20 passages.

Cell-surface markers can be identified by any suitable conventional technique, usually based on a positive/negative selection; for example, monoclonal antibodies against cell-surface markers, whose presence/absence in the cells is to be confirmed, can be used; although other techniques can also be used. Thus, in a particular embodiment, monoclonal antibodies against one, two, three, four, five, six, seven of or preferably all of CD11b, CD11c, CD14, CD45, HLAII, CD31, CD34 and CD133 are used in order to confirm the absence of said markers in the selected cells; and monoclonal antibodies against one, two, three, four, of or preferably all of CD9, CD44, CD54, CD90 and CD105 are used in order to confirm the presence thereof or detectable expression levels of, at least one of and preferably all of, said markers. Said monoclonal antibodies are known, commercially available or can be obtained by a skilled person in the art by conventional methods.

IFN-γ-inducible IDO activity in the selected cells can be determined by any suitable conventional assay. For example, the selected cells can be stimulated with IFN-γ and assayed for IDO expression; then conventional Western-blot analysis for IDO protein expression can be performed and IDO enzyme activity following IFN-γ stimulation of the selected cells can be measured by tryptophan-to-kynurenine conversion with for example via High Performance Liquid Chromatography (HPLC) analysis and photometric determination of kynurenine concentration in the supernatant as the readout. Since the ASC express IDO under certain conditions, any suitable technique which allows the detection of IDO activity following IFN-γ stimulation may be used for selecting the ASC. The amount of IDO produced depends on the number of cells per square centimeter, which is preferably at a level of 5000 cells/cm$^2$ or more, but not limited to this concentration and the concentration of IFN-gamma, which ideally is 3 ng/ml or more, but not limited to this concentration. The activity of IDO produced under the described conditions will result in a detectable production of kynurenine in the micro M range after 24 hours or more.

The capacity of the selected cells to differentiate into at least two cell lineages can be assayed by conventional methods as known in the art.

ASC can be clonally expanded, if desired, using a suitable method for cloning cell populations. For example, a proliferated population of cells can be physically picked and seeded into a separate surface (or the well of a multi-well plate). Alternatively, the cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). Of course, the cells can be cloned by plating them at low density (e.g., in a Petri dish or other suitable substrate) and isolating them from other cells using devices such as a cloning rings. The production of a clonal population can be expanded in any suitable culture medium. In any event, the isolated cells can be cultured to a suitable point when their developmental phenotype can be assessed.

It has been shown that ex vivo expansion of the ASC without inducing differentiation can be accomplished for extended time periods for example by using specially screened lots of suitable serum (such as fetal bovine serum or human serum). Methods for measuring viability and yield are known in the art (e.g., trypan blue exclusion).

Any of the steps and procedures for isolating the cells of the cell population of the invention can be performed manually, if desired. Alternatively, the process of isolating such cells can be facilitated and/or automated through one or more suitable devices, examples of which are known in the art.

MSC Cell Culture.

Said MSC are also capable of being expanded ex vivo. That is, after isolation, said MSC can be maintained and allowed to proliferate ex vivo in a cell culture medium. Such medium is composed of, for example, Dulbecco's Modified Eagle's Medium (DMEM), with antibiotics (for example, 100 units/ml Penicillin and 100 μg/ml Streptomycin) or without antibiotics, and 2 mM glutamine, and supplemented with 2-20% fetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), porcine serum, sheep serum, rabbit serum, rat serum (RS), etc. It is also within the scope of the invention that if said MSC are of human origin, the cell culture medium is supplemented with a human serum, preferably of autologous origin. It is understood that sera can be heat-inactivated at 55-65° C. if deemed necessary to inactivate components of the complement cascade. Modulation of serum concentrations and/or withdrawal of serum from the culture medium can also be used to promote survival of one or more desired cell types. Preferably, said MSC will benefit from FBS concentrations of about 2% to about 25%. In another embodiment, the MSC can be expanded in a cell culture medium of definite composition, in which the serum is replaced by a combination of serum albumin, serum transferrin, selenium, and recombinant proteins including but not limited to insulin, platelet-derived growth factor (PDGF), and basic fibroblast growth factor (bFGF) as known in the art.

Many cell culture media already contain amino acids, however some require supplementation prior to culturing of cells. Such amino acids include, but are not limited to, L-alanine, L-arginine, L-aspartic acid, L-asparagine, L cysteine, L-cystine, L-glutamic acid, L-glutamine, L-glycine, and the like.

Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone(R)), ampicillin, gentamicin, bleomycin, hygromacin, kanamycin, mitomycin, etc.

Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

Expanded Cells.

In one embodiment the MSC, regulatory T-cells and/or fibroblast cells may have been expanded prior to use in the method of the present invention. Methods for cell expansion are known in the art.

Genetically Engineered Cells

In another embodiment the MSC, regulatory T-cells and/or fibroblast cells may be genetically engineered cells (e.g. transduced or transfected with an exogenous nucleic acid), or derived therefrom.

For example said cells may be genetically engineered to constitutively express indoleamine 2,3-dioxygenase (IDO), e.g., by transfection with an appropriate nucleic acid construct encoding said enzyme and optionally a suitable promoter sequence. Genetic engineering of cells is known in the art and may be carried out by a person skilled in the art.

Irradiated Cells.

In yet another embodiment the MSC, regulatory T-cells and/or fibroblast cells may have been irradiated prior to their use in the method of the present invention. Irradiation of cells reduces their proliferative capabilities and survival times.

The irradiation may be carried out using a suitable controlled source of ionizing radiation, such a gamma irradiator device. The irradiation conditions must be experimentally adjusted by a person skilled in the art to determine the required exposure time to impart a radiation dose that causes the long term growth arrest of the MSC, regulatory T-cells and/or fibroblast cells. In one embodiment said radiation dose is within a range selected from the group consisting of 1-100 Gy; 5-85 Gy, 10-70 Gy, 12-60 Gy, however, it is particularly preferred that said radiation dose is within the range of 15-45 Gy.

CD26 Antagonist Treated Cells.

In still another embodiment the MSC, regulatory T-cells and/or fibroblast cells may be treated with a CD26 antagonist or inhibitor prior to use in the method of the present invention. CD26 antagonists and inhibitors are known in the art and include but are not limited to Aminomethylpyridine; P32/98; NVP DPP728; PSN9301; Isoleucine thiazolidide; Denagliptin; Sitagliptin; Vildagliptin; Saxagliptin; Alogliptin; Diprotin A, and such treatment may be carried out by a person skilled in the art.

IFN-Gamma Stimulated Cells.

In another embodiment the MSC, regulatory T-cells and/or fibroblast cells may be stimulated with interferon gamma prior to use in the method of the present invention. IFN-gamma treatment of MSC for the stimulation thereof is known in the art and may be carried out by a person skilled in the art.

Antigen Stimulated Cells

In still another embodiment the MSC, regulatory T-cells and/or fibroblast cells may be stimulated with antigens prior to use in the method of the present invention. Antigen treatment of MSC for the stimulation thereof is known in the art and may be carried out by a person skilled in the art.

Mitomycin C Treated MSC.

In yet another embodiment the MSC, regulatory T-cells and/or fibroblast cells may be treated with Mitomycin C prior to use in the method of the present invention. Mitomycin C treatment of MSC is known in the art and may be carried out by a person skilled in the art.

Furthermore, if desired, the MSC, regulatory T-cells and/or fibroblast cells can be subjected to a combination of two or three of the treatments selected from the group consisting of irradiation, IFN-gamma stimulation and Mitomycin C treatment prior to use in the method of the present invention.

The maintenance conditions of said MSC can also contain cellular factors that allow cells to remain in an undifferentiated form. It is apparent to those skilled in the art that prior to differentiation, supplements that inhibit cell differentiation must be removed from the culture medium. It is also apparent that not all cells will require these factors. In fact, these factors may elicit unwanted effects, depending on the cell type.

The features and advantages of the invention are more fully illustrated by the following non-limiting examples, wherein all parts and percentages are by weight, unless otherwise expressly stated.

EXAMPLE 1

Treatment of Collagen-Induced Arthritis (CIA) with ASCs

Materials and Methods

Collagen Induced Arthritis (CIA) Mouse Model

Experimental arthritis was induced in DBA1/(H-2q) male mice (6-8 weeks of age). On the day of commencement of the study, each mouse was injected subcutaneously in the tail (2-3 cm from the body) with the first dose of an emulsion of chicken type II collagen (CII) (1 mg/ml final concentration) in complete Freund's adjuvant (*Mycobacterium Tuberculosis* 1 mg/ml final concentration) (CFA) in a volume of 0.1 ml/animal. 21 days after the first injection of collagen, a second injection (booster) of CII (0.1 ml/animal) was administered to each animal, again subcutaneously in the tail but at a different location from the first injection. On this occasion the collagen suspension was made using Incomplete Freund's adjuvant (IFA).

When the arthritis score index was around 2-4 the animals were treated with expanded adipose derived stem cells or with the vehicle (Ringer's solution) as control. The evolution of CIA was followed daily (Monday to Friday) by measuring the inflammation-redness-ankylosis of the joints of upper and lower limbs, according to a pre-established scoring system.

The volume of both hind paws of each animal was measured daily after the administration of the test item or vehicle and the mean for both paws calculated. Furthermore the hind paw volume measured on day 1 (prior to first collagen injection and taken as basal volume) for each animal was subtracted from the paw volume measured on each day afterwards to obtain the net increase in paw volume (or oedema) for each animal. Additionally, the severity of the arthritis was scored with the same frequency and timing in both front and hind paws according to the following arthritis index scoring system:

0: No signs of arthritis
1: Swelling and/reddening of the paw or 1 digit
2: Two groups of joints inflamed (swelling and/or reddening)
3: More than two groups of joints inflamed (swelling and/or reddening)
4: Inflammation of the whole paw. Severe arthritis The final score is the sum of the scores for the four paws. The maximum score is 16.

Experimental Design
 Control
Group A=No treatment.
 Intravenous Administration
Group C=Intravenous injection of 1 million cells per dose, one dose per consecutive day. 5 doses in total.
Group D=Intravenous injection of 3 million cells first dose and 1 million cells on second and third dose, one dose per alternate day. 3 doses in total.
 Intralymphatic Administration
Group E=Intralymphatic injection of 320,000 cells per dose (160,000 right inguinal node, 160,000 left one). 2 doses in total, second dose 7 days prior to first.
 Vehicle Control
Group F=Intralymphatic injection of Ringer's solution. 2 doses in total, second dose 7 days prior to first.
 N=12 mice/group.
 Intravenous Administration The test item was administered intravenously via the tail vein with the use of a sterile butterfly needle (25G). The animals received 5 consecutive doses or 3 alternative days (one per day). Animals received 0.2 ml of test item as an infusion at a rate of 0.05 ml/min intravenously via the tail vein.

Intralymphatic Administration in Inguinal Lymph Nodes

DBA1 mice were anaesthetized by inhalation of 2.0 to 2.5% Isofloran via nose mask and bedded on a warming plate at 37° C. After depilation (Veet sensitive depilatory cream) and disinfection of the inguinal region with 70% ethanol, a 6 to 8 mm incision was made in the inguinal region. Lymph nodes within the inguinal fat were localized and 8 μl of vehicle or vehicle with ASCs (at a density of 20 million cells/ml) were injected into the lymph node using a Hamilton syringe with a 30 gauge needle. Incision was sutured by one or two knots and the procedure was repeated in the inguinal lymph node in the other side. Mice were allowed to recover from anaesthesia. After seven days, the procedure was repeated.

Expanded Adipose Derived Stem Cell Preparation

Human adipose tissue was obtained by liposuction, under local anaesthesia and general sedation. A hollow blunt-tipped cannula was introduced into the subcutaneous space through a small incision (less than 0.5 cm in diameter). With gentle suction, the cannula was moved through the adipose tissue abdominal-wall compartment for mechanical disruption of the fatty tissue. A saline solution and the vasoconstrictor epinephrine were injected into the adipose tissue compartment to minimize blood loss. In this way, 80 to 100 ml of raw lipoaspirate were obtained from each patient to be treated.

The raw lipoaspirate was washed extensively with sterile phosphate-buffered saline (PBS; Gibco BRL, Paisley, Scotland, UK) to remove blood cells, saline and local anaesthetic. The extracellular matrix was digested with a solution of type II collagenase (0.075%; Gibco BRL) in balanced salt solution (5 mg/ml; Sigma, St. Louis, USA) for 30 minutes at 37° C. to release the cellular fraction. Then the collagenase was inactivated by addition of an equal volume of cell culture medium (Dulbecco's modified Eagle's medium (DMEM; Gibco BRL) that contained 10% fetal bovine serum (FBS; Gibco BRL). The suspension of cells was centrifuged at 250×g for 10 minutes. Cells were resuspended in 0.16 M $NH_4Cl$ and allowed to stand for 5 minutes at room temperature (RT) for lysis of erythrocytes. The mixture was centrifuged at 250×g, and cells were resuspended in DMEM plus 10% FBS and 1% ampicillin/streptomycin mixture (Gibco BRL) and then they were filtered through a 40 μm mesh and were plated in tissue culture flasks at a concentration of $10-30\times10^3$ cells/cm².

Cells were cultured for 24 hours at 37° C. in an atmosphere of 5% $CO_2$ in air. Then, the culture flasks were washed with PBS to remove non-adhering cells and cell fragments. The cells were maintained in culture in the same medium and under the same conditions until they reached approximately 80% confluence, with replacement of the culture medium every 3 to 4 days. Cells were then passaged with trypsin-EDTA (Gibco BRL) at a dilution of 1:3 which corresponds to a cell density of approximately about $5-6\times10^3$ cells/cm².

For the experiments, cells at a duplication doubling of 12-16 were trypsinized and resuspended at the desired cell density in the vehicle (Ringer's solution). Then transferred to the syringe and injected into the mice.

Statistical Analysis

The statistical significance of the results was evaluated using the statistics program GraphPad Instat 3. Results are expressed as the mean±standard error of the mean, where (n) is the number of animals.

Figure 1:
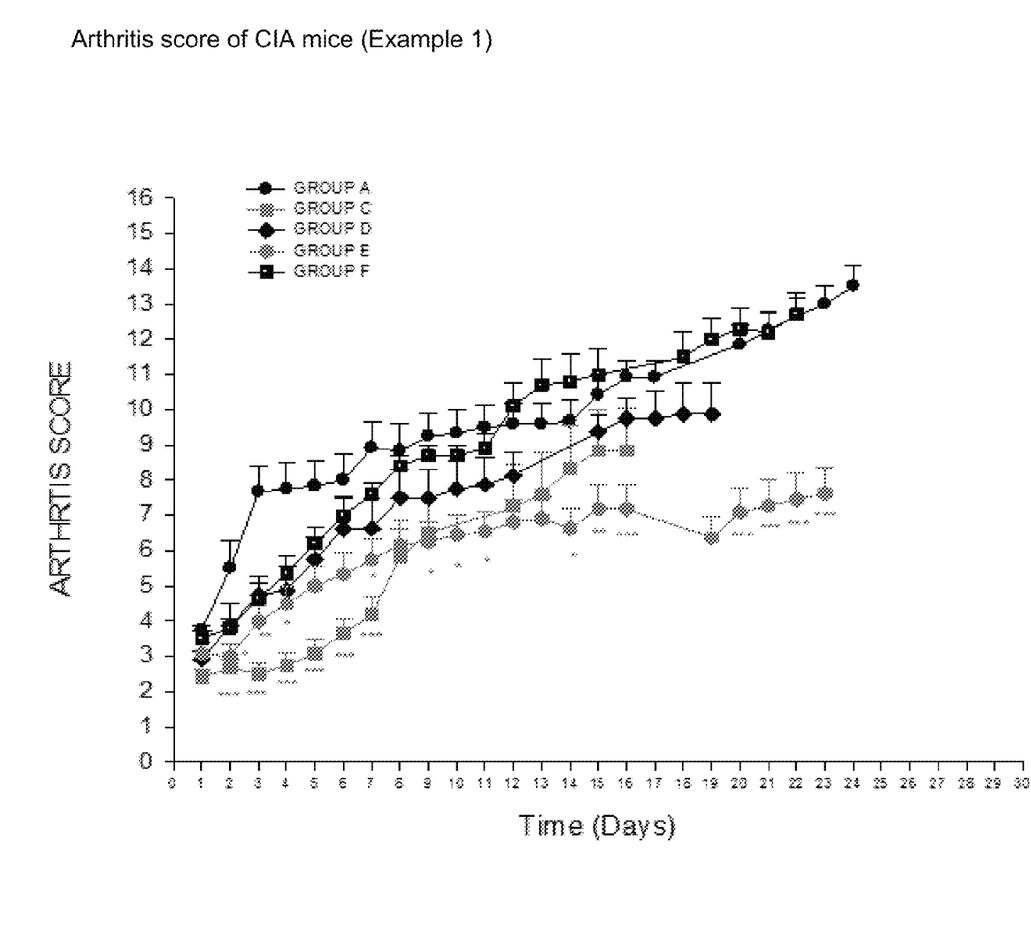
FIG. 1 illustrates that the administration of expanded adipose derived stem cells decreases the arthritis score in a collagen-induced arthritis mouse model and that intralymphatic administration is more therapeutically effective than the intravenous route. Group A: control untreated; Group C: 1 million ASCs administered IV on 5 consecutive days; Group D: 3 million ASCs administered first day and 1 million ASCs administered on days 3 and 5; Group E: 320,000 ASCs administered intralymphatically on days 1 and 7; Group F: vehicle administered intralymphatically on days 1 and 7.

FIG. 1 is annotated to illustrate the p-values of a comparison of Group A vs Group E. Significant differences are denoted as: *P<0.05, P<0.01, *P<0.001. The difference between groups was evaluated by the Kruskal-Wallis test for unpaired data with post-test of Dunn form multiple comparisons. A value of P<0.05 was taken as significant.

Results

Arthritis was induced in DBA1 mice by injection of chicken collagen II. When mice showed an arthritis score of 2-4 they were treated with expanded ASCs by intravenous or intralymphatic route. As a control for the intralymphatic administration, mice were treated with the vehicle. The arthritis score was monitored daily (see Table 1). Whereas untreated mice or mice treated with vehicle showed high inflammation of the paws that increased in a time dependent manner, mice treated with intralymphatically-delivered expanded ASCs showed significantly reduced inflammation. Moreover, the therapeutic effect of intralymphatic administration was higher than the intravenous administration (see FIG. 1).

CONCLUSION

The present study shows that intralymphatic administration of human ASCs to DBA1 mice results in a statistically significant reduction of the severity of arthritis (as indicated by arthritis index score).

Moreover, the therapeutic effect of the intralymphatic administration of a total of 640,000 ASCs (in two doses) was significantly higher than the intravenous administration of a total of 5 million cells. These results indicate that the intralymphatic route of administration is more efficacious as a higher therapeutic effect is reached with a lower number of cells.

Accordingly, while the invention has been described herein in reference to specific aspects, features and illustrative embodiments of the invention, it will be appreciated that the utility of the invention is not thus limited, but rather extends to and encompasses numerous other aspects, features, and embodiments. Accordingly, the claims hereafter set forth are intended to be correspondingly broadly construed, as including all such aspects, features, and embodiments, within their spirit and scope.

We claim:

1. A method for treatment of immune-mediated inflammatory disorders, in a subject having one or more symptoms associated with said disorders, which comprises direct delivery to a lymphatic organ of said subject a therapeutically effective amount of a composition comprising mesenchymal stem cells.

2. The method according to claim 1, wherein the composition is administered to a peripheral lymphatic organ.

3. The method of claim 2 wherein said peripheral lymphatic organ is a lymph node.

4. The method of claim 3 wherein said lymph node is an axillary or inguinal lymph node.

5. The method of claim 1 wherein said administration is carried out by means of a syringe.

TABLE 1

Arthritis score of CIA mice (Example 1)

| Group | Arthritis score measurement | DAY 1 | 2 | 3 | 4 | 5 | 6 | 7 | 8 | 9 | 10 | 11 | 12 |
|---|---|---|---|---|---|---|---|---|---|---|---|---|---|
| A | Mean | 3.75 | 5.5 | 7.67 | 7.75 | 7.83 | 8 | 8.92 | 8.83 | 9.25 | 9.33 | 9.5 | 9.58 |
|   | SD | 0.45 | 2.65 | 2.61 | 2.53 | 2.55 | 2.49 | 2.57 | 2.66 | 2.18 | 2.23 | 2.24 | 2.15 |
|   | SEM | 0.13 | 0.76 | 0.75 | 0.73 | 0.74 | 0.72 | 0.74 | 0.77 | 0.63 | 0.64 | 0.65 | 0.62 |
| C | Mean | 2.42 | 2.67 | 2.5 | 2.75 | 3.08 | 3.67 | 4.17 | 5.83 | 6.5 | 0 | 0 | 7.25 |
|   | SD | 0.67 | 0.78 | 1.09 | 1.29 | 1.44 | 1.37 | 1.75 | 2.72 | 3.48 | 0 | 0 | 4.18 |
|   | SEM | 0.19 | 0.22 | 0.31 | 0.37 | 0.42 | 0.4 | 0.51 | 0.79 | 1 | 0 | 0 | 1.21 |
| D | Mean | 2.92 | 3.88 | 4.75 | 4.88 | 5.75 | 6.63 | 6.63 | 7.5 | 7.5 | 7.75 | 7.88 | 8.13 |
|   | SD | 0.79 | 1.73 | 1.49 | 1.96 | 1.75 | 2.39 | 2.39 | 2.27 | 2.27 | 2.19 | 2.17 | 1.89 |
|   | SEM | 0.23 | 0.61 | 0.53 | 0.69 | 0.62 | 0.84 | 0.84 | 0.8 | 0.8 | 0.77 | 0.77 | 0.67 |
| E | Mean | 3.08 | 3 | 4 | 4.5 | 5 | 5.33 | 5.75 | 6.17 | 6.25 | 6.45 | 6.55 | 6.82 |
|   | SD | 1 | 1.13 | 1.48 | 1.62 | 1.91 | 2.06 | 2.05 | 2.33 | 1.96 | 1.81 | 1.81 | 2.04 |
|   | SEM | 0.29 | 0.33 | 0.43 | 0.47 | 0.55 | 0.59 | 0.59 | 0.67 | 0.57 | 0.55 | 0.55 | 0.62 |
| F | Mean | 3.5 | 3.82 | 4.64 | 5.36 | 6.2 | 7 | 7.6 | 8.4 | 8.7 | 8.7 | 8.9 | 10.1 |
|   | SD | 0.8 | 0.75 | 1.43 | 1.57 | 1.55 | 1.63 | 0.97 | 0.97 | 0.95 | 0.82 | 1.29 | 2.13 |
|   | SEM | 0.23 | 0.23 | 0.43 | 0.47 | 0.49 | 0.52 | 0.31 | 0.31 | 0.3 | 0.26 | 0.41 | 0.67 |

| Group | Arthritis score measurement | DAY 13 | 14 | 15 | 16 | 17 | 18 | 19 | 20 | 21 | 22 | 23 | 24 |
|---|---|---|---|---|---|---|---|---|---|---|---|---|---|
| A | Mean | 9.58 | 9.67 | 10.4 | 10.9 | 10.9 | 0 | 0 | 11.8 | 12.3 | 12.7 | 13 | 13.5 |
|   | SD | 2.15 | 2.06 | 1.98 | 1.68 | 1.68 | 0 | 0 | 2.04 | 1.76 | 1.83 | 1.76 | 1.98 |
|   | SEM | 0.62 | 0.59 | 0.57 | 0.48 | 0.48 | 0 | 0 | 0.59 | 0.51 | 0.53 | 0.51 | 0.57 |
| C | Mean | 7.58 | 8.33 | 8.83 | 8.83 |   |   |   |   |   |   |   |   |
|   | SD | 4.19 | 4.31 | 4 | 4.13 |   |   |   |   |   |   |   |   |
|   | SEM | 1.21 | 1.25 | 1.15 | 1.19 |   |   |   |   |   |   |   |   |
| D | Mean | 0 | 0 | 9.38 | 9.75 | 9.75 | 9.88 | 9.88 |   |   |   |   |   |
|   | SD | 0 | 0 | 1.3 | 1.58 | 2.19 | 2.47 | 2.47 |   |   |   |   |   |
|   | SEM | 0 | 0 | 0.46 | 0.56 | 0.77 | 0.88 | 0.88 |   |   |   |   |   |
| E | Mean | 6.91 | 6.64 | 7.18 | 7.18 | 0 | 0 | 6.36 | 7.09 | 7.27 | 7.45 | 7.64 |   |
|   | SD | 2.07 | 1.86 | 2.32 | 2.36 | 0 | 0 | 1.91 | 2.26 | 2.41 | 2.54 | 2.38 |   |
|   | SEM | 0.62 | 0.56 | 0.7 | 0.71 | 0 | 0 | 0.58 | 0.68 | 0.73 | 0.77 | 0.72 |   |
| F | Mean | 10.7 | 10.8 | 11 | 0 | 0 | 11.5 | 12 | 12.3 | 12.2 | 12.7 |   |   |
|   | SD | 2.31 | 2.44 | 2.31 | 0 | 0 | 2.27 | 1.94 | 1.89 | 1.81 | 2 |   |   |
|   | SEM | 0.73 | 0.77 | 0.73 | 0 | 0 | 0.72 | 0.61 | 0.6 | 0.57 | 0.63 |   |   |

6. The method of claim 5, further comprising the step of using a radiological, ultrasound or imaging device to monitor the location of an injection needle.

7. The method of claim 1, wherein the disorder is selected from the group consisting of rheumatoid arthritis, inflammatory bowel disease and multiple sclerosis.

8. The method of claim 1, wherein the mesenchymal stem cells are adipose-derived mesenchymal stem cells.

9. The method of claim 1, wherein the mesenchymal stem cells are bone marrow mesenchymal stem cells.

* * * * *